(12) United States Patent
Bogdanovich et al.

(10) Patent No.: US 11,408,784 B2
(45) Date of Patent: Aug. 9, 2022

(54) FLEXIBLE CIRCUIT DESIGN FOR MONITORING PHYSICAL BODIES

(71) Applicant: CIPHER SKIN, Denver, CO (US)

(72) Inventors: Phillip Bogdanovich, Evergreen, CO (US); Craig Weller, Evergreen, CO (US); Shaka Joaquin Doyle Bahadu, Emeryville, CA (US)

(73) Assignee: CIPHER SKIN, Denver, CO (US)

( * ) Notice: Subject to any disclaimer, the term of this patent is extended or adjusted under 35 U.S.C. 154(b) by 151 days.

(21) Appl. No.: 16/825,623

(22) Filed: Mar. 20, 2020

(65) Prior Publication Data

US 2020/0300718 A1 Sep. 24, 2020

Related U.S. Application Data

(60) Provisional application No. 62/820,877, filed on Mar. 20, 2019.

(51) Int. Cl.
| | |
|---|---|
| *G01L 1/22* | (2006.01) |
| *H05K 1/02* | (2006.01) |
| *H05K 1/14* | (2006.01) |
| *H05K 1/18* | (2006.01) |
| *H05K 1/09* | (2006.01) |

(52) U.S. Cl.
CPC ............ *G01L 1/22* (2013.01); *H05K 1/028* (2013.01); *H05K 1/095* (2013.01); *H05K 1/147* (2013.01); *H05K 1/189* (2013.01); *H05K 2201/10151* (2013.01)

(58) Field of Classification Search
CPC .......... G01L 1/22; H05K 1/028; H05K 1/095; H05K 1/147; H05K 1/189; H05K 2201/10151
USPC ......................................... 361/778
See application file for complete search history.

(56) References Cited

U.S. PATENT DOCUMENTS

| | | | |
|---|---|---|---|
| 8,640,549 B2* | 2/2014 | Inamori | G01L 1/2293 73/766 |
| 2004/0262737 A1 | 12/2004 | Haba | |
| 2011/0005845 A1 | 1/2011 | Hotelling et al. | |
| 2013/0324041 A1 | 12/2013 | Pagani | |
| 2015/0129276 A1 | 5/2015 | Shumaker et al. | |
| 2016/0306481 A1* | 10/2016 | Filiz | G01L 1/146 |
| 2020/0294907 A1* | 9/2020 | Dardona | H01L 21/76895 |

* cited by examiner

*Primary Examiner* — Binh B Tran
(74) *Attorney, Agent, or Firm* — Lorenz & Kopf, LLP (57) ABSTRACT

A flexible circuit may be provided that allows for the monitoring of a physical object. The flexible circuit includes a plurality of flexible conductive segments that are disposed in a geometric pattern. The flexible conductive segments include nodes, and the physical object is monitored by analyzing changes in electrical resistance in the conductive segments between the nodes. The flexible circuit may also include sensors disposed on the nodes for monitoring additional conditions. A processor monitors the flexible conductive segments and sensors, and may provide an output regarding the status of the physical object.

20 Claims, 8 Drawing Sheets

FLEXIBLE CIRCUIT DESIGN FOR MONITORING PHYSICAL BODIES

RELATED PATENTS

This application claims priority to U.S. Patent Application No. 62/820,877, filed on Mar. 20, 2019, which is incorporated by reference as if fully set forth herein. This application hereby incorporates by reference in its entirety U.S. Patent Appl. Pub. No. 2019-0046114A1 to Bogdanovich et al., filed Jul. 30, 2018.

BACKGROUND OF THE INVENTION

Embodiments disclosed herein relate to a flexible circuit system and methodologies used for monitoring physical properties of a physical body attached to the system. Certain embodiments disclosed herein relate to a single large flexible circuit that can be created by interconnecting multiple flexible circuit modules.

There are multiple types of sensors and flexible circuits currently in use. Such sensors and/or circuits, however, may require specific designs based on their intended use. Changing the intended use and/or adapting the sensor or circuit to changes in its use may necessitate a redesign of the component that may take days, weeks, or even longer. For example, alterations to an ECG monitor may be made in a lab to change the monitor from monitoring respiration on two planes in four locations and a 12-lead ECG to measuring respirations at twelve points in three dimensions and a 51-lead ECG. Making these changes to the monitor may take a circuit, and probably a system redesign as well a physical change to the device being worn. Making such changes may a substantial amount of time and be costly to make (including costs associated with the time to make the changes).

Thus, there is a need for a modular flexible circuit system that can be applied to a variety of different scenarios where simultaneous monitoring of complex motion/position in space, along with other metrics is desired. It may be desirable for such a system to be simple to incorporate and easily modifiable and/or scalable to a particular use-case scenario. The system may also be inexpensive and readily adaptable in a short time span (e.g., in a matter of minutes or hours).

Based on the foregoing, currently existing technologies and processes associated with monitoring the physical properties of physical bodies may be improved upon so as to provide increased functionality and reliability for users. In particular, such enhancements may provide for reduced expenses for users and businesses, enhanced monitoring capabilities, more accurate monitoring, increased adaptability, among other benefits.

SUMMARY

A flexible circuit that allows for the monitoring of a physical object is provided. The flexible circuit may include a plurality of flexible conductive segments that are disposed in a geometric or other desired pattern. In certain embodiments, the flexible conductive segments may include nodes. The physical object may be monitored by analyzing changes in electrical resistance in the conductive segments between the nodes. The flexible circuit may also include sensors disposed on the nodes for monitoring additional conditions. A processor may monitor the flexible conductive segments and sensors, and may provide an output regarding the status of the physical object.

In an embodiment, a flexible circuit module is disclosed. The flexible circuit module may include an electrically insulating substrate. Additionally, the flexible circuit module may include a conductive layer that may be positioned on the substrate. In certain embodiments, the conductive layer may comprise at least two conductive elements positioned along a path between a first node and a second node in the conductive layer. In certain embodiments, the first node and the second node may be located at different positions on the substrate. In certain embodiments, the at least two conductive elements may be electrically coupled to the first node and the second node, and the at least two conductive elements may be electrically insulated from each other along the path between the first node and the second node.

In another embodiments, a flexible circuit is disclosed. The flexible circuit may include at least three nodes. Additionally, the flexible circuit may include conductive elements connecting each of the nodes such that the nodes and the conductive elements form a geometric shape. In certain embodiments, the conductive elements may pass electronic signals between the nodes. The flexible circuit may also include a processor that may be configured to monitor the electronic signals passed between the nodes.

BRIEF DESCRIPTION OF THE DRAWINGS

Features and advantages of the methods and apparatus described herein will be more fully appreciated by reference to the following detailed description of presently preferred but nonetheless illustrative embodiments when taken in conjunction with the accompanying drawings in which.

While the disclosure is susceptible to various modifications and alternative forms, specific embodiments thereof are shown by way of example in the drawings and will herein be described in detail. It should be understood, however, that the drawings and detailed description thereto are not intended to limit the disclosure to the particular form illustrated, but on the contrary, the intention is to cover all modifications, equivalents and alternatives falling within the spirit and scope of the present disclosure as defined by the appended claims. The headings used herein are for organizational purposes only and are not meant to be used to limit the scope of the description. As used throughout this application, the word "may" is used in a permissive sense (i.e., meaning having the potential to), rather than the mandatory sense (i.e., meaning must). Similarly, the words "include," "including," and "includes" mean including, but not limited to. Additionally, as used in this specification and the appended claims, the singular forms "a", "an", and "the" include singular and plural referents unless the content clearly dictates otherwise The term "coupled" means directly or indirectly connected.

The scope of the present disclosure includes any feature or combination of features disclosed herein (either explicitly or implicitly), or any generalization thereof, whether or not it mitigates any or all of the problems addressed herein. Accordingly, new claims may be formulated during prosecution of this application (or an application claiming priority thereto) to any such combination of features. In particular, with reference to the appended claims, features from dependent claims may be combined with those of the independent claims and features from respective independent claims may be combined in any appropriate manner and not merely in the specific combinations enumerated in the appended claims.

DETAILED DESCRIPTION OF EMBODIMENTS

The following examples are included to demonstrate preferred embodiments. It should be appreciated by those of skill in the art that the techniques disclosed in the examples which follow represent techniques discovered by the inventor to function well in the practice of the disclosed embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosed embodiments.

This specification includes references to "one embodiment" or "an embodiment." The appearances of the phrases "in one embodiment" or "in an embodiment" do not necessarily refer to the same embodiment, although embodiments that include any combination of the features are generally contemplated, unless expressly disclaimed herein. Particular features, structures, or characteristics may be combined in any suitable manner consistent with this disclosure.

Figure 1:
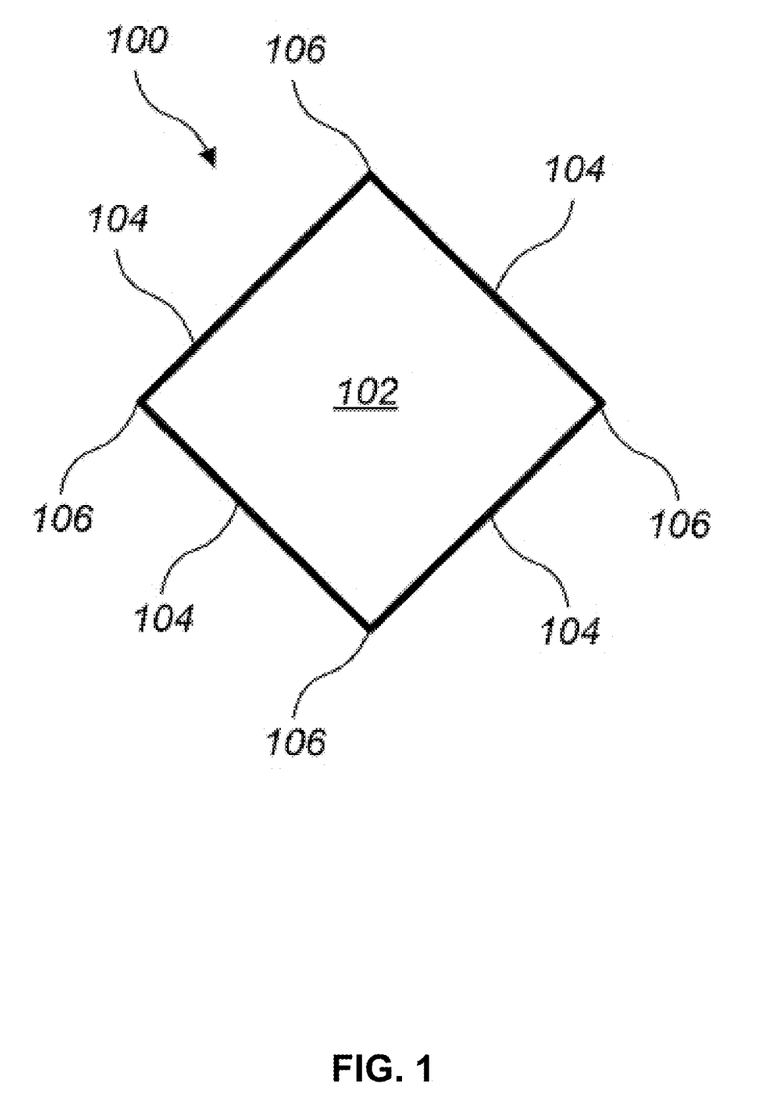
FIG. 1 depicts a plan view representation of an embodiment of a circuit module.

FIG. 1 depicts a plan view representation of an embodiment of circuit module 100. In certain embodiments, the module 100 includes substrate 102 with one or more conductive segments 104 coupled between nodes 106 on the substrate. Module 100 may have a geometric shape and/or any other desired shape. For example, in one embodiment, as shown in FIG. 1, module 100 (e.g., substrate 102) has a diamond shape. Other geometric shapes with vertices (e.g., corners) may also be contemplated such as, but not limited to, squares, rectangles, and/or other regular quadrilateral shapes. Geometric shapes may be three-dimensional, where the dimensions may include length, width, height, and thickness.

In certain embodiments, conductive segments 104 are positioned on the edges of substrate 102 and nodes 106 are positioned at the vertices of the substrate 102. As shown in FIG. 1, conductive segments 104 may intersect at nodes 106. As such, nodes 106 may be connection points between conductive segments 104. In certain embodiments, the nodes 106 and/or the conductive segments 104 may be positioned at other locations of the substrate 102

In certain embodiments, substrate 102 is a non-conductive (e.g., electrically insulating) flexible substrate. For example, substrate 102 may be a non-conductive flexible polymer or elastomer (e.g., a thin, non-conductive polymer film). Conductive segments 104 may include conductive polymers. The conductive polymers may be, for example, conductive plastic, conductive elastomer, and/or another material that conducts electricity, can be distorted, and/or is pliable. Conductive segments 104 may be able to transfer data and have a resistance that is measurable. The resistance of conductive segments 104 may be altered by changing the physical characteristics of the polymer (e.g., width, depth, and/or length of the polymer).

Figure 2:
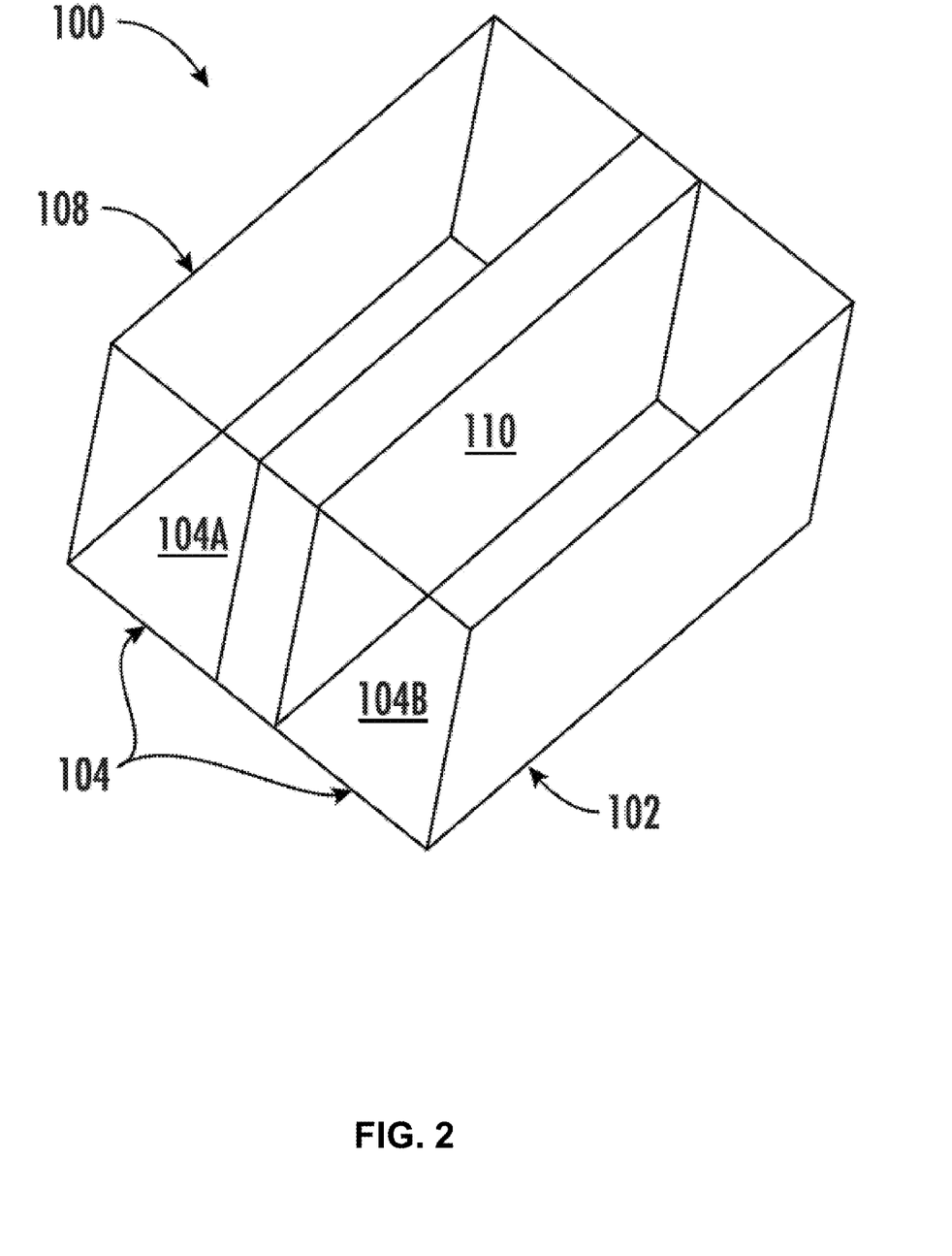
FIG. 2 depicts an expanded view of an embodiment of a portion of a circuit module.

As shown in FIG. 1, conductive segments 104 may be positioned on top of substrate 102. FIG. 2 depicts an expanded view of an embodiment of a portion of module 100 showing a portion of conductive segment 104 on substrate 102. In certain embodiments, top layer 108 is placed over conductive segments 104 on substrate 102. In some embodiments, conductive segments 104 are made of conductive polymer that is thin (relatively flat) and flexible. Top layer 108 may be, for example, an electrically insulating (non-conductive) layer similar such as a non-conductive polymer. Top layer 108 may have similar electrical properties to substrate 102. In one contemplated embodiment for forming module 100, conductive segments 104 are formed on substrate 102 and then top layer 108 is formed over the conductive segments on the substrate to encapsulate or enclose the conductive segments. Thus, conductive segments 104 may be encapsulated or enclosed between substrate 102 and top layer 108 to electrically insulate the conductive segments from the ambient environment outside module 100.

In certain embodiments, as shown in FIG. 2, conductive segment 104 includes two conductive portions 104A, 104B. Conductive portions 104A, 104B may be electrically isolated (electrically separated) by insulating section 110. Thus, conductive portions 104A, 104B may be electrically separated along a length of conductive segment 104 between nodes 106 in module 100. Insulating section 110 may be, for example, a build-up section of insulating material between conductive portions 104A, 104B. In some embodiments, insulating section 110 is formed as part of substrate 102 and/or top layer 108. For example, insulating section 110 may be a portion of substrate 102 untreated as conductive portions 104A, 104B are formed on the substrate. Top layer 108 may then be formed over conductive portions 104A, 104B and insulating section 110 to finish formation of module 100. In some embodiments, insulating section 110 is formed separate from substrate 102 and/or top layer 108.

In certain embodiments, insulating section 110 has a selected height and/or width. The height and/or width of insulating section 110 may be selected to prevent arcing or shorting between conductive portions 104A, 104B (e.g., maintain electrical isolation between the conductive portions). Insulating section 110, along with substrate 102 and top layer 108, may provide electrical insulation for conductive segments 104 (and conductive portions 104A, 104B) that maintains signal quality and prevents arcing, shorting, and/or noise along the conductive segments.

In certain embodiments, module 100 includes one or more conductive segments 104 that include electrically separated conductive portions 104A, 104B, as described above. Conductive segments 104 may include electrically separated conductive portions 104A, 104B to allow the conductive segments to transmit electrical current, including alternating (AC) and direct current (DC). For example, conductive portions 104A, 104B may be used as separate pathways for (+) and (−) current transmission in a DC circuit. Using electrically separated conductive portions 104A, 104B to transmit DC may allow transmission of data using power line communication (PLC) or power line communication over direct current (PLC-DC). Transmitting current and data over electrically separated conductive portions 104A, 104B allows data and current to be transmitted over a single material on a single plane (e.g., the conductive portions lie along the same plane (are in the same layer) on substrate 102). Thus, module 100 may include a thin, flexible circuit (the circuit being implemented using conductive segments 104) to provide data and current distribution in a single plane with the conductive elements of the module (e.g., the conductive segments) being fully electrically insulated. Such modules 100 may be thin, relatively easy to manufacture, and more consistent in electrical properties through the elastic distortion of the materials in the module.

In certain embodiments, as shown in FIG. 1, module 100 includes four conductive segments 104 (with each conductive segment having conductive portions 104A, 104B) connected between four nodes 106 with substrate 102 having a diamond (rotated square) shape. The design of module 100 may allow multiple modules to be interconnected together to scale up the circuit architecture (e.g., the circuit of conductive segments 104 and nodes 106) to any size desired for a particular application while maintaining electromechanical properties of the individual modules. In some embodiments, the interconnected modules may share conductive segments 104 along shared edges between modules.

Figure 3:
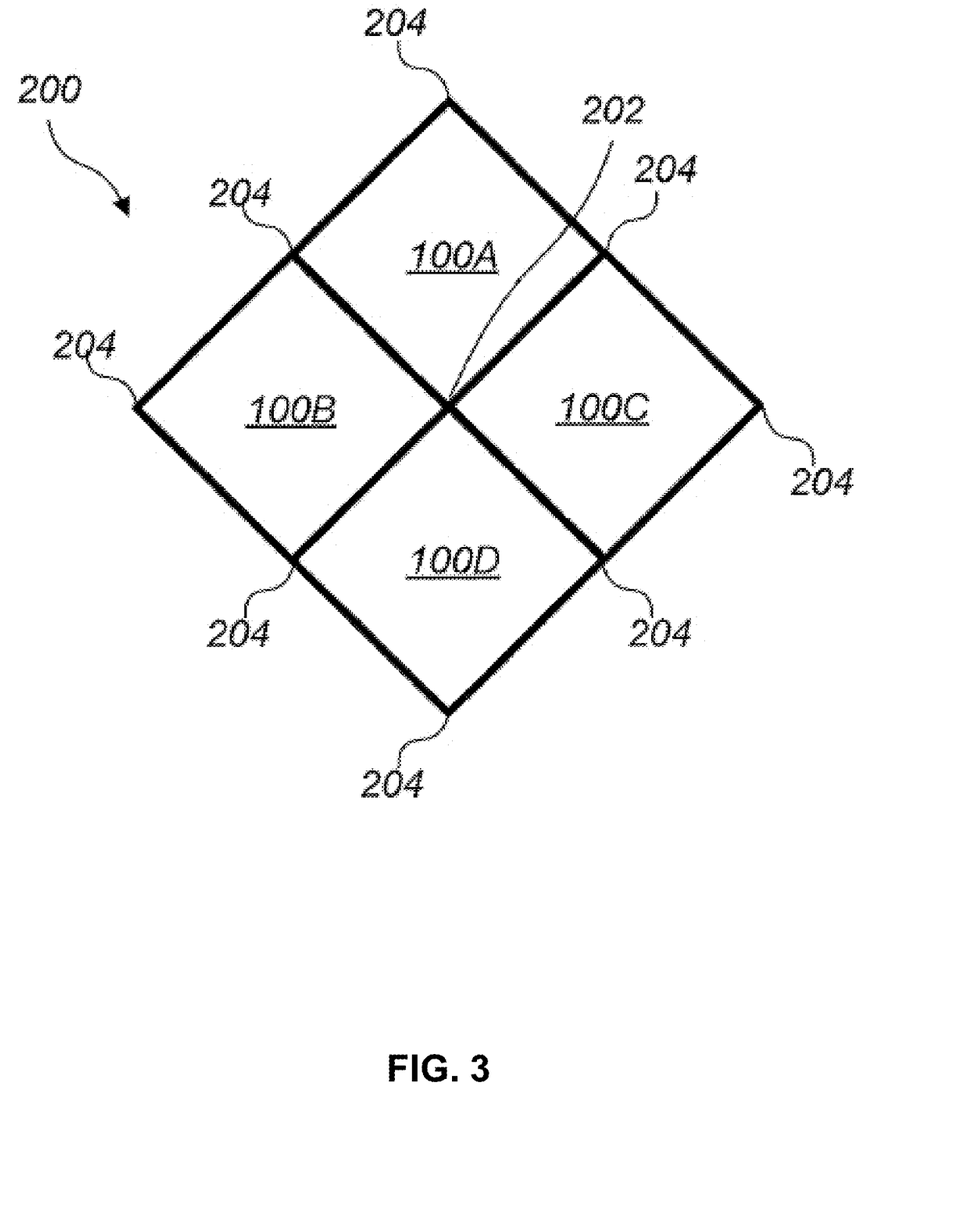
FIG. 3 depicts a plan view representation of an embodiment of interconnected circuit modules.

FIG. 3 depicts a plan view representation of an embodiment of interconnected circuit modules. Frame 200 may include four interconnected circuit modules 100A, 100B, 100C, 100D. In some embodiments, frame 200 is a minimum arrangement of modules 100 where the distributive, mechanical, and electrical characteristics of the modules can be shared at any scale. Other arrangements of modules 100 may also be possible where the distributive, mechanical, and electrical characteristics of the modules can be shared at any scale.

Frame 200 may include vertex 202 and vertices 204. Vertex 202 and vertices 204 may be intersection points between nodes 106 of modules 100. Conductive segments 104 may intersect at vertex 202 and vertices 204. Vertex 202 may be at the center of frame 200 where four conductive segments 104 intersect. Vertices 204 may be on the edges of frame 200 where two or three conductive segments 104 intersect. Vertices 204 may, however, be capable of intersecting up to four segments (if, for example, additional modules are added to frame 200).

Figure 4:
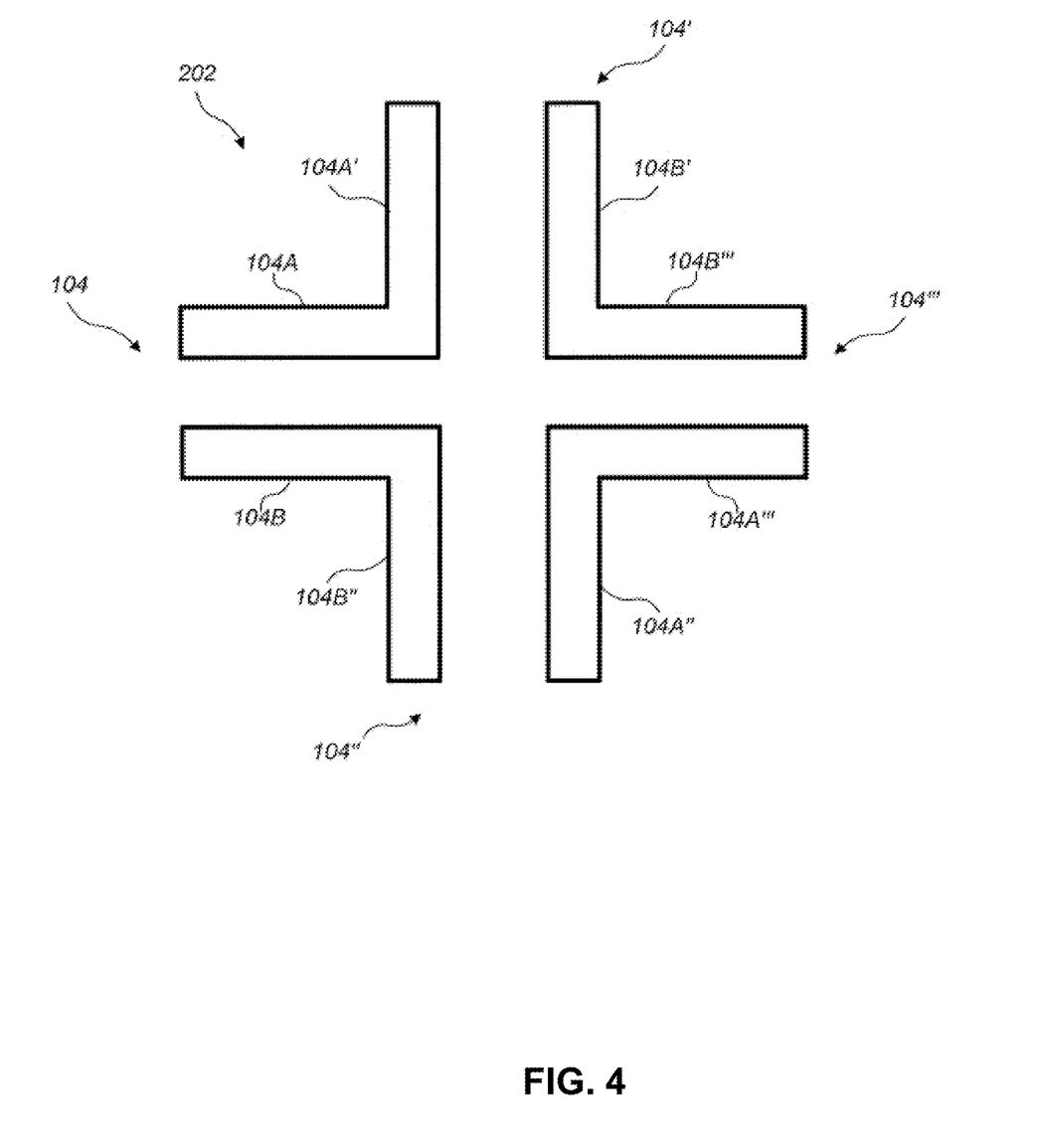
FIG. 4 depicts a plan view representation of an embodiment of a vertex.

FIG. 4 depicts a plan view representation of an embodiment of vertex 202. Vertex 202 may have four intersection conductive sections 104, 104', 104", 104'". Each conductive section 104 includes corresponding conductive portions 104A, 104B where, in this embodiment, conductive portions 104A are (+) portions and conductive portions 104B are (−) portions. At vertex 202, the polarity of a conductive segment may be opposite the conductive segment that follows or precedes it (along a path through the vertex). For example, as shown in FIG. 4, conductive section 104 has opposite polarity to conductive section 104'" and conductive section 104' has opposite polarity to conductive section 104".

Having alternating polarities in the conductive sections may allow a complete circuit to be formed in frame 200 (or any set of interconnected modules). The complete circuit may be formed as positive and negative charges are continuous through vertex 202. For example, as shown in FIG. 4, conductive portion 104A' continues from conductive portion 104, conductive portion 104B'" continues from conductive portion 104B', conduction portion 104B" continues from conductive portion 104B, and conductive portion 104A'" continues from conductive portion 104A". While the embodiment of FIG. 4 depicts that conductive portions 104A are (+) portions and conductive portions 104B are (−) portions, it is to be understood that conductive portions 104A, 104B may have no fixed polarity when module 100 and/or frame 200 is constructed and that the polarity of the conductive portions (and conductive segments 104) may have polarities determined by the application used with the modules.

In some embodiments, one or more sensors are placed at vertex 202 and/or vertices 204 (e.g., at the location of nodes 106). The sensors may be, for example, detection units, measurement units, and/or other units capable of detecting electrical signals from conductive segments 104. The sensors may be located to create a data packet on the current being passed at each specific sensor (e.g., vertices) from conductive segments 104. The data packet may include a time at which a current is measured. The sensors may send the measured information to a processor associated with the sensors located on module 100, on frame 200, or remotely.

As described herein, conductive segments 104 and nodes 106 (e.g., the vertices) may combine to create circuits in module 100 and/or frame 200. Electricity passing through the circuit may be continuously monitored by the sensors (or other attached devices). The electricity passing through the circuit may be monitored for distortion of conductive segments 104 (e.g., distortion of the conductive polymers). Distortion indicates expansion and contraction in the circuit and may be defined by change(s) in electrical properties of conductive segments 104 (e.g., changes in resistance, voltage, and/or conduction that occurs when the material is stretched and when it is returning to a normal resting state). The change in electrical properties may be defined as the alteration in electrical properties that occurs when the circuit is distorted from a resting state to an apex state, and then returns to a resting state. The changes in electrical properties during this process (e.g., distortion) may be defined by a known formula related in some way to the principal relational formula between resistance/voltage/conduction.

In some embodiments, the sensors may be capable of receiving current and/or data from conductive segments 104 and passing the current and/or data through the sensor. Some sensors (such as sub-sensors) may be capable of monitoring a vast array of metrics. For example, the sensors may be used to monitor specific metrics such as, but not limited to, ambient temperature, surface temperature on the object (e.g., physical structure) being monitored, strain, torque and torsion, expansion and contraction, flow, physical position, orientation, etc.

Figure 5:
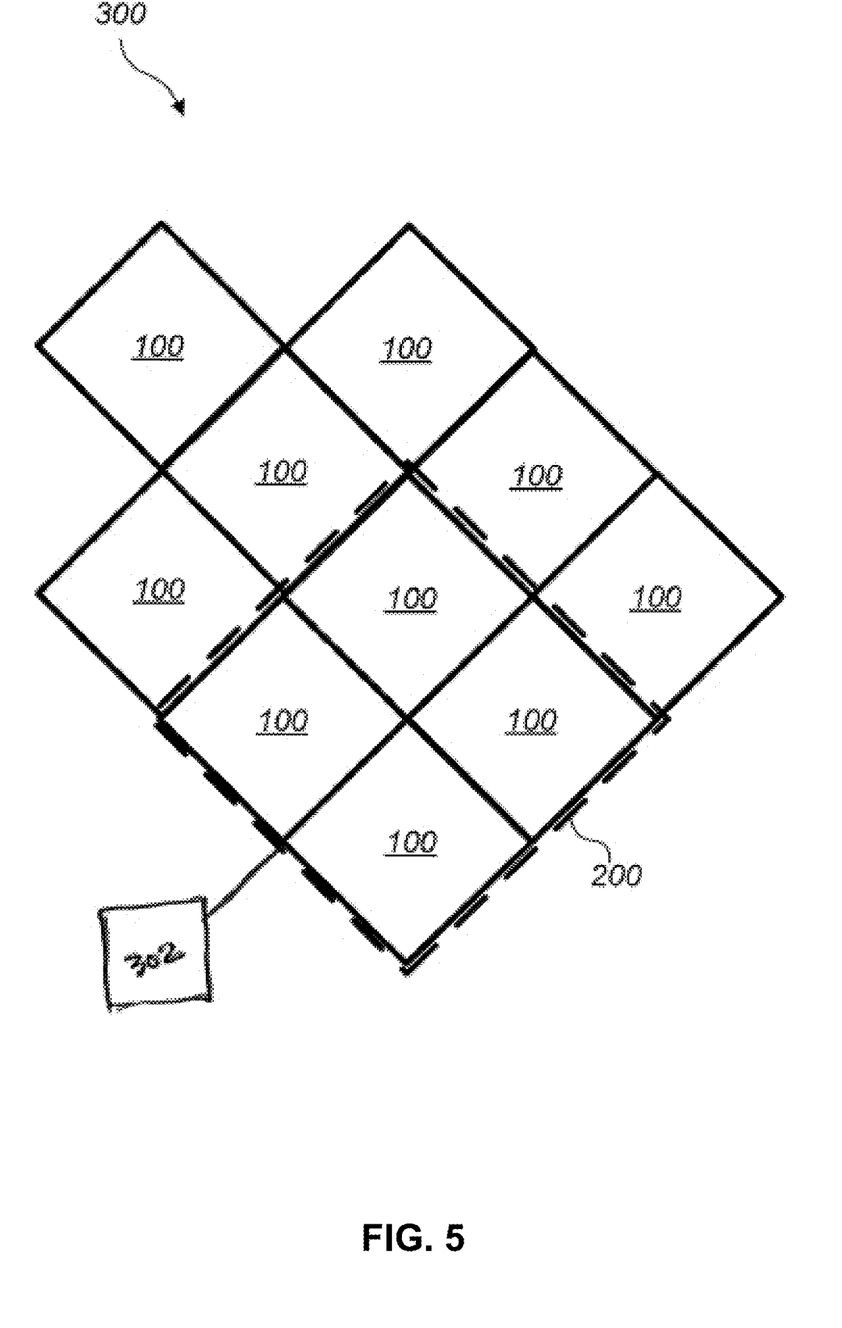
FIG. 5 depicts a plan view representation of another embodiment of interconnected circuit modules.

FIG. 5 depicts a plan view representation of another embodiment of interconnected circuit modules. Lattice 300 may include a combination of one or more frames 200 (the frames may be full frames or part frames) and/or modules 100. Lattice 300 may be used to cover a surface for an application of modules 100 (as described herein). Lattice 300 may be scalable to any size lattice to distribute power and data in a manner that can be defined geometrically. In some embodiments, lattice 300 may include modules 100 with varying sizes and/or shapes. For example, lattice 300 may include a varied series of triangular modules.

A system for monitoring physical properties of a physical body attached to the system may be generated using the concepts of lattice 300 (and modules 100 and/or frame 200).

The modularity of modules 100 allows for lattice 300 to be built-up from the generic modules for each particular application rather than needing to design a completely different circuit for each particular application. For example, the recurring geometry of modules 100 may be used to design lattice 300 having a desired shape and size for a particular application of the monitoring system by selecting the appropriate number of modules and putting them into the correct shape for the application. Thus, any shape or size of garment (or another application of the system) may be accommodated by simply making (e.g., printing) more modules with the need to design a separate circuit for each application.

The shape and size of lattice 300 in two dimensions and/or three dimensions for an application may be determined based on the needs for the application. The shape and size of lattice 300, including lattice thickness, may be determined by the area that needs to be covered and/or the physical properties to be evaluated. For example, lattice 300 may have a different size and shape for being used with socks than for being used with a shirt, a pair of shorts, or a horse blanket. Lattice 300 may also have difference size and shape when used to monitor non-biological physical objects, such as pipes or structural surfaces. As such, lattice 300 may be added to any garment or other physical structure regardless of the size of the garment or physical structure. Additionally, lattice 300 may be added to any garment or physical structure regardless of how the lattice is applied to the garment or physical structure. For example, lattice 300 may be adhered to the inside of a garment or the lattice may be attached to a surface of a physical structure.

Lattice 300 may be adapted to a particular application by forming the desired size and shape of the lattice from modules 100 and placing the necessary sensors and/or sub-sensors on the lattice for the particular application. Thus, lattice 300 may be generated for a particular application in a short amount of time (on the order of minutes or an hour or other desired time interval). A monitoring system using lattice 300 may be used in a variety of applications for monitoring of complex motion and/or position in space plus other metrics. In some instances, lattice 300 may be used to replace traditional wiring harnesses in biological monitoring systems and monitor biometric properties. In some instances, lattice 300 may be affixed to the walls of structural systems to monitor integrity and predict failure of the structural systems. The flexible nature of lattice 300 (e.g., the circuit) may allow the monitoring system to be comfortable and as close to universally applicable as possible. The utilization of conductive elastomers in lattice 300 may allow the monitoring system to be adhered directly to an object (e.g., a garment or physical structure) and become part of the object's structure.

In some embodiments, lattice 300 may be implemented into a garment. Lattice 300 may be scaled to different shapes and/or sizes for use in a variety of different garment applications. For example, lattice 300 may be implemented in shorts, shirts, socks, hats, etc. to monitor performance and/or health of the wearer of the garment. Lattice 300 may allow for power and data to be distributed on the same plane, which may reduce garment thickness and increase flexibility and pliability compared to other monitoring systems. Lattice 300 may also be implemented in other textiles (e.g., soft items) for use in non-garment related systems. Such other textiles may include any application where the monitoring system (e.g., the circuit of lattice 300) needs to be flexible, flat, modular, and capable of transferring data along with power.

Lattice 300 may also be used in non-biological systems (e.g., any physical structure with a surface that is non-biologic). Examples of non-biological systems include, but are not limited to, the walls of a building, the bulkhead or hull of a ship, a bridge, or the walls of a nuclear reactor. Monitoring such non-biological systems using lattice 300 may be provided to observe for integrity and detect structural or use deterioration prior to a critical failure.

In certain embodiments, the monitoring system includes a computer processor and/or processor-related components 302. Related components may include, for example, a system BUS of some type, memory, wired and wireless transmission modules, a power line communication transmitter/receiver (PLC TX/RX), and a solid-state transmission decoder/transmitter (e.g., RFID). Using the processor and one or more of the related components may allow the monitoring system to provide both on-board and off-board data aggregation and initial analysis. For example, a wireless transmitter may be used to provide wireless communication between the monitoring system and a remote device (e.g., a mobile device). In some embodiments, a component in the monitoring system includes a battery. The battery may be, for example, a flexible battery such as a plastic composite battery or another battery that is combustion resistant, inexpensive to manufacture, thin, and/or light in weight.

Although specific embodiments have been described above, these embodiments are not intended to limit the scope of the present disclosure, even where only a single embodiment is described with respect to a particular feature. Examples of features provided in the disclosure are intended to be illustrative rather than restrictive unless stated otherwise. The above description is intended to cover such alternatives, modifications, and equivalents as would be apparent to a person skilled in the art having the benefit of this disclosure.

Figure 6:
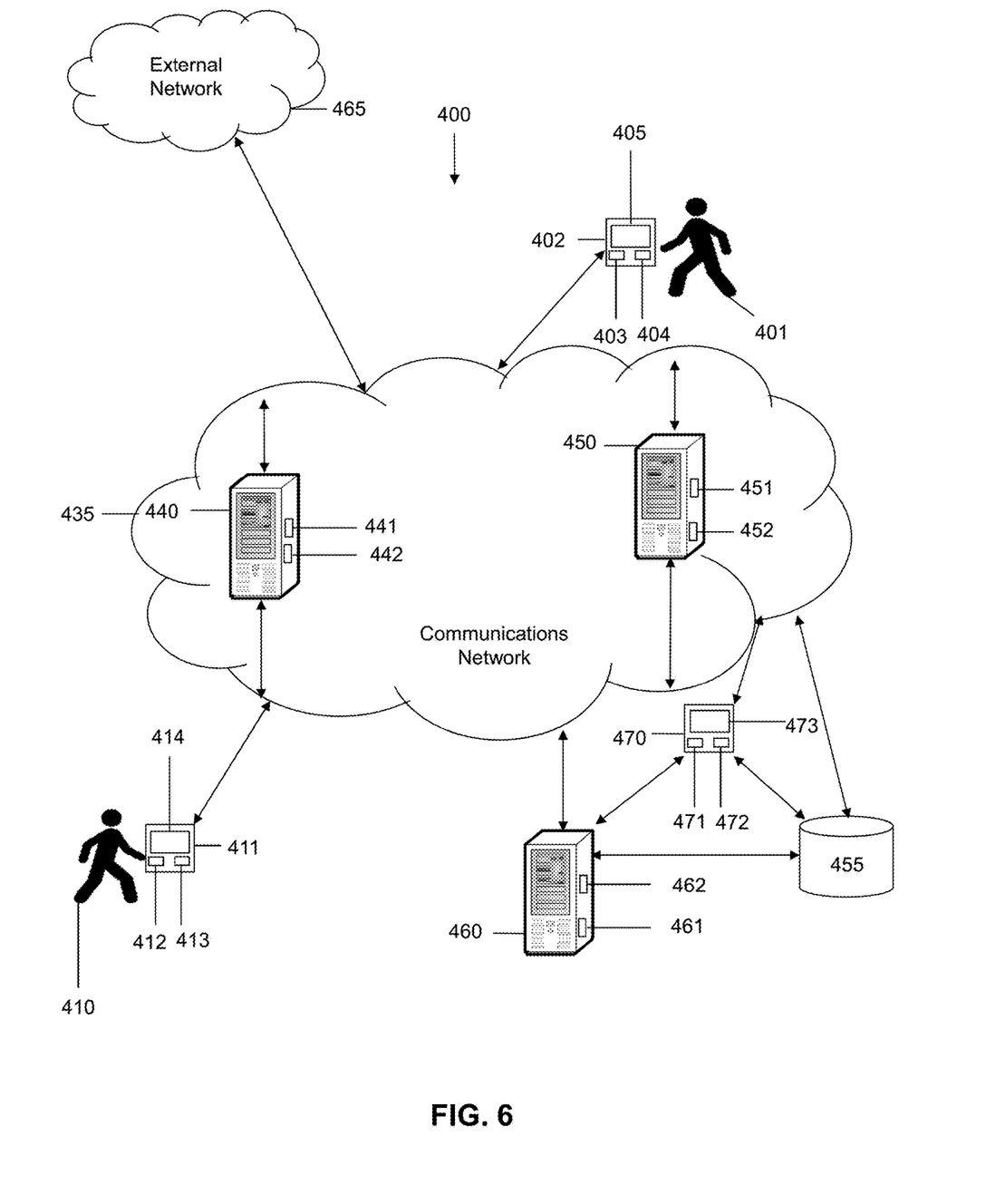
FIG. 6 is a schematic diagram of a system that may be utilized to monitor physical bodies by utilizing a flexible circuit design according to an embodiment of the present disclosure.

In certain embodiments, the flexible circuit module 100, the frame 200, the lattice 300, the monitoring system, the sensors, and/or any of the componentry of FIGS. 1-5 may be communicatively linked with a system 400 and/or be incorporated into the system 400, as shown in FIG. 6. The system 400 may be configured to perform any of the functionality performed by the flexible circuit module 100, the frame 200, the lattice 300, the monitoring system, and/or any of the componentry of FIGS. 1-5. Additionally, the system 400 may be configured to perform operations and/or functionality offloaded by flexible circuit module 100, the frame 200, the lattice 300, the monitoring system, and/or any of the sensors described in the present disclosure. For example, in certain instances, the computing, storage, and/or other resources of the monitoring system may be overloaded or may be nearing a threshold level that warrants offloading operations and functionality to the system 400 to assist the monitoring system in completing various operations and to increase performance of the monitoring system. Notably, any of the components of flexible circuit module 100, the frame 200, the lattice 300, the monitoring system, and/or sensors may be configured to communicate with any of the components of the system 400, such as via a wired connection, wireless connection, any other type of connection, or a combination thereof. In certain embodiments, the system 400 may form a part of the monitoring system, the flexible circuit module 100, the frame 200, the lattice 300, and/or any of the sensors.

The system 400 may be configured to support, but is not limited to supporting, monitoring applications and services, sensor-based applications and services, wearable device applications and services, health monitoring applications and services, communication applications and services, alert applications and services, data and content services, data aggregation applications and services, big data technologies, data synthesis applications and services, data analysis applications and services, computing applications and services, cloud computing services, interne services, satellite services, telephone services, software as a service (SaaS) applications, mobile applications and services, and any other computing applications and services. The system 400 may include a first user 401, who may utilize a first user device 402 to access data, content, and applications, or to perform a variety of other tasks and functions. In certain embodiments, the first user 401 may be a user that is seeking to monitor conditions associated with a physical object and/or body, such as an oil pipeline, a building, and/or any other physical structure. In certain embodiments, the first user 401 may be a user that is seeking to monitor conditions associated with himself and/or possibly other users.

The first user device 402 utilized by the first user 401 may include a memory 403 that includes instructions, and a processor 404 that executes the instructions from the memory 403 to perform the various operations that are performed by the first user device 402. In certain embodiments, the processor 404 may be hardware, software, or a combination thereof. The first user device 402 may also include an interface 405 (e.g. screen, monitor, graphical user interface, audio device interface, etc.) that may enable the first user 401 to interact with various applications executing on the first user device 402, to interact with various applications executing within the system 400, and to interact with the system 400 itself. In certain embodiments, the first user device 402 may be a computer, a laptop, a tablet device, a phablet, a server, a mobile device, a smartphone, a smart watch, and/or any other type of computing device. Illustratively, the first user device 402 is shown as a mobile device in FIG. 6. The first user device 402 may also include a global positioning system (GPS), which may include a GPS receiver and any other necessary components for enabling GPS functionality, accelerometers, gyroscopes, sensors, and any other componentry suitable for a mobile device. In certain embodiments, the first user device 402 may be configured to include any number of sensors, such as, but not limited to, temperature sensors, pressure sensors, motion sensors, light sensors, oxygen sensors, heart rate sensors, touch sensors, proximity sensors, gas sensors, acoustic sensors, chemical sensors, acceleration sensors, humidity sensors, moisture sensors, presence sensors, force sensors, any type of sensors, or a combination thereof. In certain embodiments, the first user device 402 may be configured to communicate with any of the components of the flexible circuit module 100, the frame 200, the lattice 300, the monitoring system, the sensors, and/or any of the components of FIGS. 1-8.

In addition to the first user 401, the system 400 may include a second user 410, who may utilize a second user device 411 to access data, content, and applications, or to perform a variety of other tasks and functions. As with the first user 401, the second user 410 may be a user that is seeking to monitor a physical object and/or body, such as a building, a vehicle, and/or any other physical object or structure. However, in certain embodiments, the second user 410 may be a supervisor of the first user 401, a colleague of the first user 401, and/or any other type of user. Much like the first user 401, the second user 410 may utilize second user device 411 to access an application (e.g. a browser or a mobile application) executing on the second user device 411 that may be utilized to access web pages, data, and content associated with the system 400. The second user device 411 may include a memory 412 that includes instructions, and a processor 413 that executes the instructions from the memory 412 to perform the various operations that are performed by the second user device 411. In certain embodiments, the processor 413 may be hardware, software, or a combination thereof. The second user device 411 may also include an interface 414 (e.g. a screen, a monitor, a graphical user interface, etc.) that may enable the second user 410 to interact with various applications executing on the second user device 411, to interact with various applications executing in the system 400, and to interact with the system 400. In certain embodiments, the second user device 411 may be a computer, a laptop, a tablet device, a phablet, a server, a mobile device, a smartphone, a smart watch, and/or any other type of computing device. Illustratively, the second user device 411 may be a computing device in FIG. 6. The second user device 411 may also include any of the componentry described for first user device 402. The second user device 411 may similarly be configured to communicate with any of the components of the flexible circuit module 100, the frame 200, the lattice 300, the monitoring system, the sensors, and/or any of the components of FIGS. 1-8.

In certain embodiments, the first user device 402 and the second user device 411 may have any number of software applications and/or application services stored and/or accessible thereon. For example, the first and second user devices 402, 411 may include applications for determining and analyzing conditions associated with monitored objects and/or physical structures, applications for analyzing sensor data, applications for determining and analyzing health conditions, applications for determining and analyzing the physiological status of a user, applications for generating alerts, applications for analyzing and interpreting sensor data, artificial intelligence applications, machine learning applications, big data applications, applications for analyzing data, applications for integrating data, cloud-based applications, search engine applications, natural language processing applications, database applications, algorithmic applications, phone-based applications, product-ordering applications, business applications, e-commerce applications, media streaming applications, content-based applications, database applications, gaming applications, internet-based applications, browser applications, mobile applications, service-based applications, productivity applications, video applications, music applications, social media applications, presentation applications, any other type of applications, any types of application services, or a combination thereof. In certain embodiments, the software applications and services may include one or more graphical user interfaces so as to enable the first and second users 401, 410 to readily interact with the software applications.

The software applications and services may also be utilized by the first and second users 401, 410 to interact with any device in the system 400, any components of the system 200, any network in the system 400, or any combination thereof. For example, the software applications executing on the first and second user devices 402, 411 may be applications for receiving data, applications for monitoring physical structures and/or bodies, applications for storing data, applications for analyzing sensor data, applications for determining health conditions, applications for determining how to respond to a health condition, applications for determining a physiological status of a user, applications for determining how to respond to an environmental condition (e.g. an environmental condition that may affect the first user 401), applications for receiving demographic and preference information, applications for transforming data, applications for executing mathematical algorithms, applications for generating and transmitting electronic messages, applications for generating and transmitting various types of content, any other type of applications, or a combination thereof. In certain embodiments, the first and second user devices 402, 411 may include associated telephone numbers, internet protocol addresses, device identities, or any other identifiers to uniquely identify the first and second user devices 402, 411 and/or the first and second users 401, 410. In certain embodiments, location information corresponding to the first and second user devices 402, 411 may be obtained based on the internet protocol addresses, by receiving a signal from the first and second user devices 402, 411, or based on profile information corresponding to the first and second user devices 402, 411.

The system 400 may also include a communications network 435. The communications network 435 of the system 400 may be configured to link each of the devices in the system 400 to one another. For example, the communications network 435 may be utilized by the first user device 402 to connect with other devices within or outside communications network 435. Additionally, the communications network 435 may be configured to transmit, generate, and receive any information and data traversing the system 400. In certain embodiments, the communications network 435 may include any number of servers, databases, or other componentry, and may be controlled by a service provider. The communications network 435 may also include and be connected to a cloud-computing network, a phone network, a wireless network, an Ethernet network, a satellite network, a broadband network, a cellular network, a private network, a cable network, the Internet, an internet protocol network, a content distribution network, any network, or any combination thereof. Illustratively, server 440 and server 450 are shown as being included within communications network 435. The communications network 435 may also be utilized to link each of the components and devices of the flexible circuit module 100, the frame 200, the lattice 300, the monitoring system, and/or any other components of FIGS. 1-8 to each other and/or to the system 400.

Notably, the functionality of the system 400 may be supported and executed by using any combination of the servers 440, 450, and 460. The servers 440, 450 may reside in communications network 435, however, in certain embodiments, the servers 440, 450 may reside outside communications network 435. The servers 440, 450 may be utilized to perform the various operations and functions provided by the system 400, such as those requested by applications executing on the first and second user devices 402, 411. In certain embodiments, the server 440 may include a memory 441 that includes instructions, and a processor 442 that executes the instructions from the memory 441 to perform various operations that are performed by the server 440. The processor 442 may be hardware, software, or a combination thereof. Similarly, the server 450 may include a memory 451 that includes instructions, and a processor 452 that executes the instructions from the memory 451 to perform the various operations that are performed by the server 450. In certain embodiments, the servers 440, 450, and 460 may be network servers, routers, gateways, switches, media distribution hubs, signal transfer points, service control points, service switching points, firewalls, routers, edge devices, nodes, computers, mobile devices, or any other suitable computing device, or any combination thereof. In certain embodiments, the servers 440, 450 may be communicatively linked to the communications network 435, any network, any device in the system 400, or any combination thereof.

The database 455 of the system 400 may be utilized to store and relay information that traverses the system 400, cache information and/or content that traverses the system 400, store data about each of the devices in the system 400, and perform any other typical functions of a database. In certain embodiments, the database 455 may store the output from any operation performed by the flexible circuit module 100, the frame 200, the lattice 300, and/or the monitoring system, operations performed and/or outputted by any component, program, process, device, network of the system 400, monitoring system, or any combination thereof. For example, the database 455 may store data from data sources, such as, but not limited to, flexible circuit module 100, frame 200, lattice 300, the monitoring system, or a combination thereof. The database 455 may store information relating to the monitored electrical resistances values, electricity passing through the sensors, changes in voltage, changes in conduction, any electrical or other properties, and any physical properties monitored by the flexible circuit module 100, the frame 200, the lattice 300, the monitoring system, and/or the system 400. In certain embodiments, the database 455 may be connected to or reside within the communications network 435, any other network, or a combination thereof. In certain embodiments, the database 455 may serve as a central repository for any information associated with any of the devices and information associated with the system 400. Furthermore, the database 455 may include a processor and memory or be connected to a processor and memory to perform the various operations associated with the database 455. In certain embodiments, the database 455 may be connected to the servers 440, 450, 460, the first user device 402, the second user device 411, any devices in the system 400, any devices of the flexible circuit module 100, the frame 200, the lattice 300, the monitoring system, any other device, any network, or any combination thereof.

The database 455 may also store information obtained from the system 400, store information associated with the first and second users 401, 410, store location information for the first and second user devices 402, 411 and/or first and second users 401, 410, store user profiles associated with the first and second users 401, 410, store device profiles associated with any device in the system 400, the flexible circuit module 100, the frame 200, the lattice 300, and/or the monitoring system, store communications traversing the system 400, store user preferences, store demographic information for the first and second users 401, 410, store information associated with any device or signal in the system 400, store information relating to usage of applications accessed by the first and second user devices 402, 411, store any information obtained from any of the networks in the system 400, store historical data associated with the first and second users 401, 410, store device characteristics, store information relating to any devices associated with the first and second users 401, 410, or any combination thereof. The database 455 may store algorithms for analyzing sensor data obtained from the flexible circuit module 100, the frame 200, the lattice 300, and/or monitoring system, algorithms for determining events, such as health conditions and/or physiological status, algorithms conducting artificial intelligence and/or machine learning, algorithms for comparing sensor data to baseline and/or threshold values, any other algorithms for performing any other calculations and/or operations in the system 400, or any combination thereof. The database 455 may also be configured to store information relating to detected conditions and/or events, actions to perform in response to the detected conditions and/or events, information indicating whether one or more of the actions have been performed, any other information provided by the system 400 and/or method 700, or any combination thereof. In certain embodiments, the database 455 may be configured to store any information generated and/or processed by the system 400, store any of the information disclosed for any of the operations and functions disclosed for the system 400 herewith, store any information traversing the system 200, or any combination thereof. Furthermore, the database 455 may be configured to process queries sent to it by any device in the system 400, the flexible circuit module 100, the frame 200, the lattice 300, and/or the monitoring system.

The system 400 may also include an external network 465. The external network 465 of the system 400 may be configured to link each of the devices in the system 400 to one another. For example, the external network 465 may be utilized by the first user device 402, the second user device 411, the flexible circuit module 100, the frame 200, the lattice 300, and/or the monitoring system to connect with other devices within or outside communications network 435. Additionally, the external network 465 may be configured to transmit, generate, and receive any information and data traversing the system 400. In certain embodiments, the external network 465 may include any number of servers, databases, or other componentry, and may be controlled by a service provider. The external network 465 may also include and be connected to a cloud-computing network, a phone network, a wireless network, an Ethernet network, a satellite network, a broadband network, a cellular network, a private network, a cable network, the Internet, an internet protocol network, a content distribution network, any network, or any combination thereof. In certain embodiments, the external network 465 may be outside the system 400 and may be configured to perform various functionality provided by the system 400, such as if the system 400 is overloaded and/or needs additional processing resources.

Notably, as shown in FIG. 6, the system 400 may perform any of the operative functions disclosed herein by utilizing the processing capabilities of server 460, the storage capacity of the database 455, or any other component of the system 400 to perform the operative functions disclosed herein. The server 460 may include one or more processors 462 that may be configured to process any of the various functions of the system 400. The processors 462 may be software, hardware, or a combination of hardware and software. Additionally, the server 460 may also include a memory 461, which stores instructions that the processors 462 may execute to perform various operations of the system 400. For example, the server 460 may assist in processing loads handled by the various devices in the system 400, such as, but not limited to, positioning conductive segments on a substrate of a flexible circuit module 100, incorporating an insulating portion onto the substrate and/or to other portions of the flexible circuit module 100; incorporating nodes into the flexible circuit module 100, incorporating any of the components of the frame 200 and/or lattice 300; incorporating sensors into the flexible circuit module 100, the frame 200, and/or the lattice 300; monitoring electricity passing through the circuits of the flexible circuit module 100, frame 200, and/or lattice 300; determining distortion of the conductive segments based on the monitoring; determining whether there is expansion and/or contraction in a circuit; determining changes in electrical properties of the circuits and/or segments; measuring various metrics associated with the physical bodies and/or objects being monitored; outputting reports indicating analyzed data and/or actions to be performed based on the analyzed data; and performing any other suitable operations conducted in the system 400 or otherwise. In one embodiment, multiple servers 460 may be utilized to process the functions of the system 400. The server 460 and other devices in the system 400, may utilize the database 455 for storing data about the devices in the system 400 or any other information that is associated with the system 400. In one embodiment, multiple databases 455 may be utilized to store data in the system 400.

In certain embodiments, the system 400 may also include a computing device 470. The computing device 470 may include one or more processors 472 that may be configured to process any of the various functions of the system 400. The processors 472 may be software, hardware, or a combination of hardware and software. Additionally, the computing device 470 may also include a memory 471, which stores instructions that the processors 472 may execute to perform various operations of the system 400. For example, the computing device 470 may assist in processing loads handled by the various devices in the system 400, such as, but not limited to, devices and components of the flexible circuit module 100, the frame 200, the lattice 300, and/or the monitoring system.

Although the figures illustrate specific example configurations of the various components of the system 400, the system 400 may include any configuration of the components, which may include using a greater or lesser number of the components. For example, the system 400 is illustratively shown as including a first user device 402, a second user device 411, a communications network 435, a server 440, a server 450, a server 460, a database 455, and an external network 465. However, the system 400 may include multiple first user devices 402, multiple second user devices 411, multiple databases 425, multiple communications networks 435, multiple servers 440, multiple servers 450, multiple servers 460, multiple databases 455, multiple external networks 465, and/or any number of any of the other components inside or outside the system 400. Similarly, the system 400 may include any number of data sources, applications, systems, and/or programs. Notably, any of the components of the system 400 may be integrated into and/or communicatively coupled to the flexible circuit module 100, the frame 200, the lattice 300, and/or the monitoring system. Furthermore, in certain embodiments, substantial portions of the functionality and operations of the system 400 may be performed by other networks and systems that may be connected to system 400.

Figure 7:
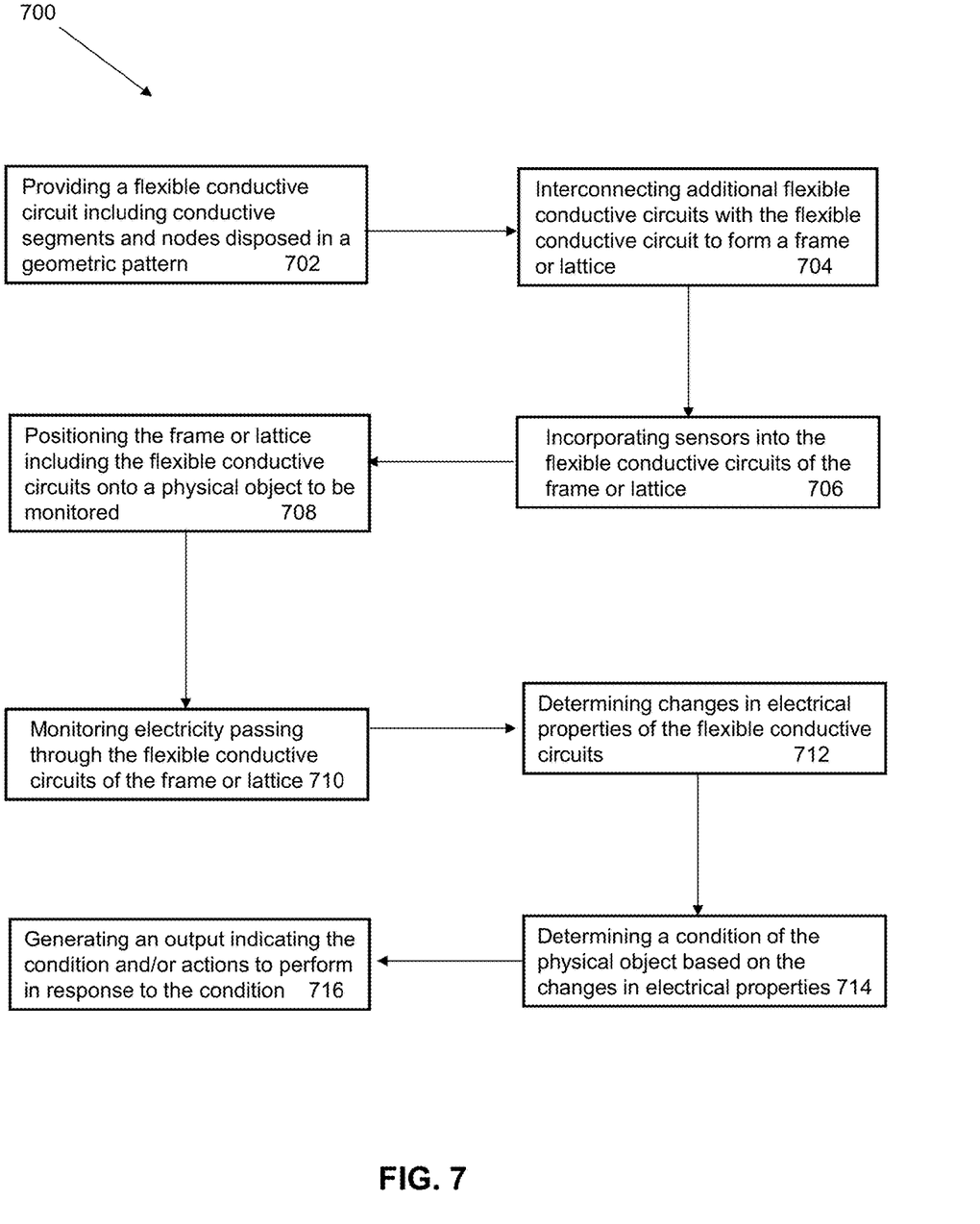
FIG. 7 is a flow diagram illustrating a sample method for monitoring physical bodies by utilizing a flexible circuit design according to an embodiment of the present disclosure.

As shown in FIG. 7, an exemplary method 700 for monitoring physical objects and/or bodies is schematically illustrated. The method 700 may include, at step 702, providing a flexible conductive circuit including conductive segments and nodes disposed in a geometric pattern. In certain embodiments, the providing may be performed and/or facilitated by utilizing any of the components of flexible circuit module 100, frame 200, lattice 300, the monitoring system, any of the components of system 400, any other components, programs, devices, and/or individuals, or a combination thereof. At step 704, the method 700 may include interconnecting additional flexible conductive circuits with the flexible conductive circuit to form a frame or lattice. In certain embodiments, the interconnecting may be performed and/or facilitated by utilizing any of the components of flexible circuit module 100, frame 200, lattice 300, the monitoring system, any of the components of system 400, any other components, programs, devices, and/or individuals, or a combination thereof.

At step 706, the method 700 may include incorporate sensors into the flexible conductive circuits of the frame or lattice. In certain embodiments, the incorporating may be performed and/or facilitated by utilizing any of the components of flexible circuit module 100, frame 200, lattice 300, the monitoring system, any of the components of system 400, any other components, programs, devices, and/or individuals, or a combination thereof. At step 708, the method 700 may include positioning the frame or lattice including the flexible conductive circuits onto a physical object to be monitored. In certain embodiments, the positioning may be performed and/or facilitated by utilizing any of the components of flexible circuit module 100, frame 200, lattice 300, the monitoring system, any of the components of system 400, any other components, programs, devices, and/or individuals, or a combination thereof.

At step 710, the method 700 may monitoring electricity passing through the flexible conductive circuits of the frame or lattice. In certain embodiments, the monitoring may be performed and/or facilitated by utilizing any of the components of flexible circuit module 100, frame 200, lattice 300, the monitoring system, any of the components of system 400, any other components, programs, devices, and/or individuals, or a combination thereof. At step 712, the method 700 may include determining changes in electrical properties of the flexible conductive circuits based on the monitoring. In certain embodiments, the determining may be performed and/or facilitated by utilizing any of the components of flexible circuit module 100, frame 200, lattice 300, the monitoring system, any of the components of system 400, any other components, programs, devices, and/or individuals, or a combination thereof. At step 714, the method 700 may include determining a condition of the physical object based on the changes in the electrical properties. In certain embodiments, the determining may be performed and/or facilitated by utilizing any of the components of flexible circuit module 100, frame 200, lattice 300, the monitoring system, any of the components of system 400, any other components, programs, devices, and/or individuals, or a combination thereof. At step 716, the method 700 may include generating an output indicating the condition and/or actions to perform in response to the determined condition of the physical object. For example, the output can indicate measured sensor data, a visual display of the data, actions to be performed with respect to the object to rectify the condition, any other actions to be performed, or a combination thereof. In certain embodiments, the generating may be performed and/or facilitated by utilizing any of the components of flexible circuit module 100, frame 200, lattice 300, the monitoring system, any of the components of system 400, any other components, programs, devices, and/or individuals, or a combination thereof.

Figure 8:
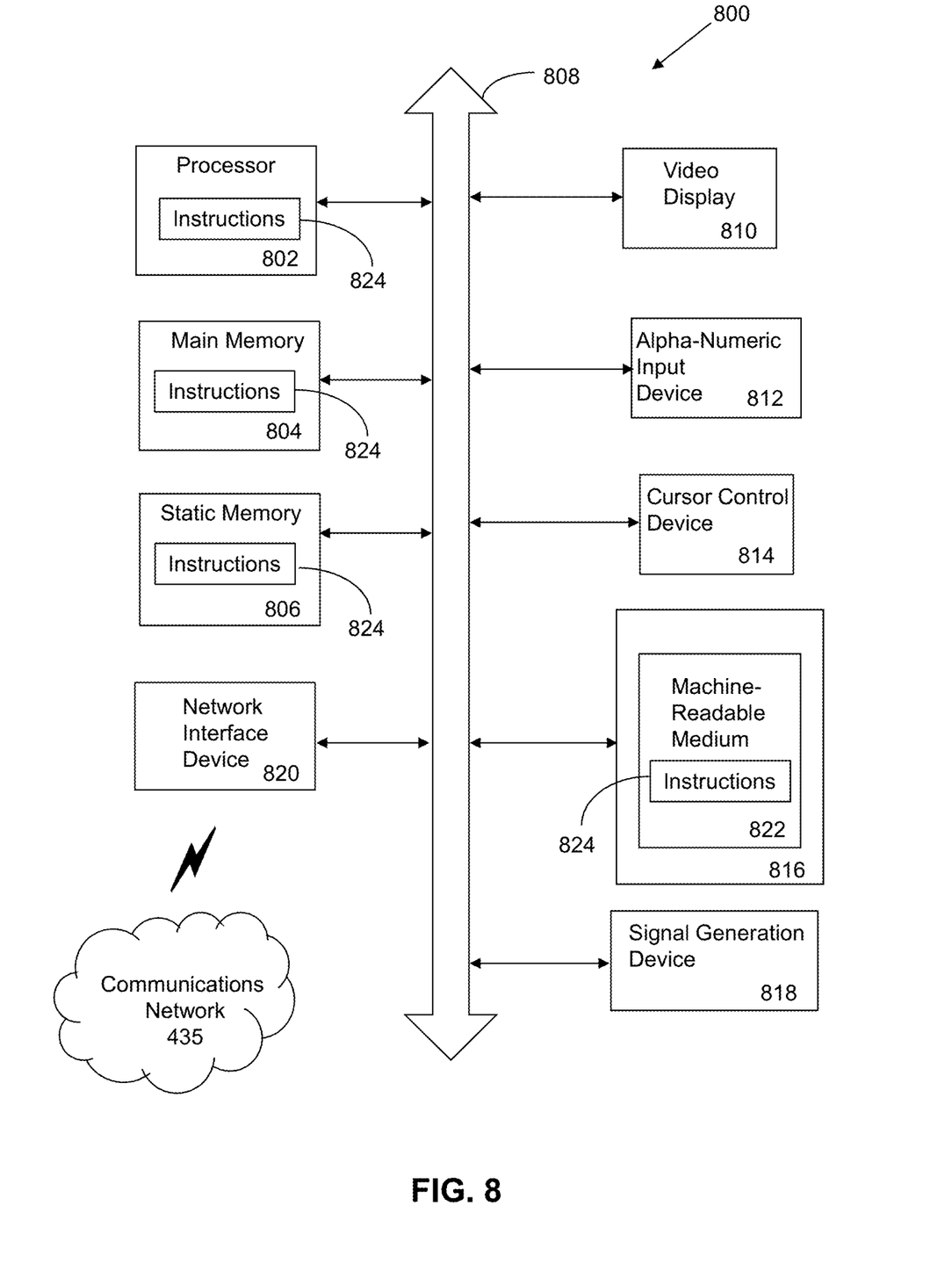
FIG. 8 is a schematic diagram of a machine in the form of a computer system within which a set of instructions, when executed, may cause the machine to perform any one or more of the methodologies or operations of the systems and methods for monitoring physical bodies by utilizing a flexible circuit design.

Referring now also to FIG. 8, at least a portion of the methodologies and techniques described with respect to the exemplary embodiments of the system 400, flexible circuit module 100, the frame 200, the lattice 300, and/or monitoring system can incorporate a machine, such as, but not limited to, computer system 800, or other computing device within which a set of instructions, when executed, may cause the machine to perform any one or more of the methodologies or functions discussed above. The machine may be configured to facilitate various operations conducted by the system 400, flexible circuit module 100, the frame 200, the lattice 300, and/or monitoring system. For example, the machine may be configured to, but is not limited to, assist the system 400 by providing processing power to assist with processing loads experienced in the system 400, by providing storage capacity for storing instructions or data traversing the system 400, or by assisting with any other operations conducted by or within the system 400.

In some embodiments, the machine may operate as a standalone device. In some embodiments, the machine may be connected (e.g., using communications network 435, another network, or a combination thereof) to and assist with operations performed by other machines, programs, functions, and systems, such as, but not limited to, the first user device 402, the second user device 411, the server 440, the server 450, the database 455, the server 460, the external network 465, the communications network 435, the flexible circuit module 100, the frame 200, the lattice 300, the monitoring system, any device, system, and/or program, or any combination thereof. The machine may be connected with any component in the system 400. In a networked deployment, the machine may operate in the capacity of a server or a client user machine in a server-client user network environment, or as a peer machine in a peer-to-peer (or distributed) network environment. The machine may comprise a server computer, a client user computer, a personal computer (PC), a tablet PC, a laptop computer, a desktop computer, a control system, a network router, switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

The computer system 800 may include a processor 802 (e.g., a central processing unit (CPU), a graphics processing unit (GPU, or both), a main memory 804 and a static memory 806, which communicate with each other via a bus 808. The computer system 800 may further include a video display unit 810, which may be, but is not limited to, a liquid crystal display (LCD), a flat panel, a solid state display, or a cathode ray tube (CRT). The computer system 800 may include an input device 812, such as, but not limited to, a keyboard, a cursor control device 814, such as, but not limited to, a mouse, a disk drive unit 816, a signal generation device 818, such as, but not limited to, a speaker or remote control, and a network interface device 820.

The disk drive unit 816 may include a machine-readable medium 822 on which is stored one or more sets of instructions 824, such as, but not limited to, software embodying any one or more of the methodologies or functions described herein, including those methods illustrated above. The instructions 824 may also reside, completely or at least partially, within the main memory 804, the static memory 806, or within the processor 802, or a combination thereof, during execution thereof by the computer system 800. The main memory 804 and the processor 802 also may constitute machine-readable media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the present disclosure, the methods described herein are intended for operation as software programs running on a computer processor. Furthermore, software implementations can include, but not limited to, distributed processing or component/object distributed processing, parallel processing, or virtual machine processing can also be constructed to implement the methods described herein.

The present disclosure contemplates a machine-readable medium 822 containing instructions 824 so that a device connected to the communications network 435, the external network 465, another network, or a combination thereof, can send or receive voice, video or data, and communicate over the communications network 435, the external network 465, another network, or a combination thereof, using the instructions. The instructions 824 may further be transmitted or received over the communications network 435, the external network 465, another network, or a combination thereof, via the network interface device 820.

While the machine-readable medium 822 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that causes the machine to perform any one or more of the methodologies of the present disclosure.

The terms "machine-readable medium," "machine-readable device," or "computer-readable device" shall accordingly be taken to include, but not be limited to: memory devices, solid-state memories such as a memory card or other package that houses one or more read-only (non-volatile) memories, random access memories, or other re-writable (volatile) memories; magneto-optical or optical medium such as a disk or tape; or other self-contained information archive or set of archives is considered a distribution medium equivalent to a tangible storage medium. The "machine-readable medium," "machine-readable device," or "computer-readable device" may be non-transitory, and, in certain embodiments, may not include a wave or signal per se. Accordingly, the disclosure is considered to include any one or more of a machine-readable medium or a distribution medium, as listed herein and including art-recognized equivalents and successor media, in which the software implementations herein are stored.

The illustrations of arrangements described herein are intended to provide a general understanding of the structure of various embodiments, and they are not intended to serve as a complete description of all the elements and features of apparatus and systems that might make use of the structures described herein. Other arrangements may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Thus, although specific arrangements have been illustrated and described herein, it should be appreciated that any arrangement calculated to achieve the same purpose may be substituted for the specific arrangement shown. This disclosure is intended to cover any and all adaptations or variations of various embodiments and arrangements of the invention. Combinations of the above arrangements, and other arrangements not specifically described herein, will be apparent to those of skill in the art upon reviewing the above description. Therefore, it is intended that the disclosure not be limited to the particular arrangement(s) disclosed as the best mode contemplated for carrying out this invention, but that the invention will include all embodiments and arrangements falling within the scope of the appended claims.

The foregoing is provided for purposes of illustrating, explaining, and describing embodiments of this invention. Modifications and adaptations to these embodiments will be apparent to those skilled in the art and may be made without departing from the scope or spirit of this invention. Upon reviewing the aforementioned embodiments, it would be evident to an artisan with ordinary skill in the art that said embodiments can be modified, reduced, or enhanced without departing from the scope and spirit of the claims described below.

What is claimed is:

1. A flexible circuit arrangement with a plurality of modular circuit modules that are interconnected together into a lattice, the flexible circuit arrangement comprising:
    an electrically insulating substrate;
    a conductive layer positioned on the substrate, wherein the conductive layer comprises a plurality of conductive elements that are interconnected at respective nodes of the lattice, the respective nodes including a first node, a second node, and a third node, the plurality of conductive elements arranged in a first branch and a second branch relative to the first node, the first branch extending along a first path between the first node and the second node, the second branch extending along a second path between the first node and the third node;
    an electrically insulating top layer placed over the conductive layer on the substrate;
        wherein the first node, the second node, and the third node are located at different positions on the substrate, wherein the first branch includes at least two first conductive element portions that are electrically coupled to the first node and the second node, wherein the at least two first conductive element portions are electrically insulated from each other along the first path between the first node and the second node;
        wherein the second branch includes at least two second conductive element portions that are electrically coupled to the first node and the third node, wherein the at least two second conductive element portions are electrically insulated from each other along the second path between the first node and the third node;
        wherein one of the at least two first conductive element portions and one of the at least two second conductive element portions are electrically connected at the first node.

2. The flexible circuit arrangement of claim 1, wherein a portion of the electrically insulating top layer is positioned between the at least two first conductive element portions.

3. The flexible circuit arrangement of claim 1, wherein the at least two first conductive element portions comprise parallel elements along the first path between the first node and the second node.

4. The flexible circuit arrangement of claim 1, wherein the at least two first conductive element portions comprise substantially flat, conductive wires made of conductive polymer.

5. The flexible circuit arrangement of claim 1, wherein the at least two first conductive element portions are configured to provide power-line communication between the first node and the second node.

6. The flexible circuit arrangement of claim 1, wherein the at least two conductive element portions are configured to transmit power and data between the first node and the second node.

7. The flexible circuit arrangement of claim 1, further comprising a sensor positioned at the first node.

8. The flexible circuit arrangement of claim 1, further comprising:
- a fourth node, the plurality of conductive elements arranged in a third branch relative to the first node, the third branch extending along a third path between the first node and the fourth node;
- wherein the third branch includes at least two third conductive element portions that are electrically coupled to the first node and the fourth node, wherein the at least two third conductive element portions are electrically insulated from each other along the third path between the first node and the fourth node; and
- wherein another of the at least two second conductive element portions and one of the at least two third conductive element portions are electrically connected at the first node.

9. The flexible circuit arrangement of claim 8, wherein the at least two first conductive element portions are configured to have opposite polarity to corresponding ones of the at least two third conductive element portions.

10. The flexible circuit arrangement of claim 1, wherein the first node, second node, and third node are configured to receive electrical signals from the plurality of conductive elements.

11. The flexible circuit arrangement of claim 1, further comprising a processor, the processor being configured to assess electrical signals in the conductive layer.

12. The flexible circuit arrangement of claim 11, wherein the processor is configured to assess changes in electrical properties of the conductive layer from the assessed electrical signals.

13. The flexible circuit arrangement of claim 12, wherein the flexible circuit arrangement may be distorted from a first state to a second state, which causes the changes in at least one of resistance, voltage, and conduction in the conductive layer, and wherein the processor is configured to assess the changes in the at least one of resistance, voltage, and conduction in the conductive layer.

14. The flexible circuit arrangement of claim 1, wherein at least one of the first node, the second node, and the third node includes a sensor disposed thereon.

15. The flexible circuit arrangement of claim 1, wherein the conductive layer is non-planar with the first node, the second node, and the third node spaced apart in three dimensions.

16. The flexible circuit arrangement of claim 1, wherein the plurality of conductive elements are comprised of a metal rubber.

17. The flexible circuit arrangement of claim 1, wherein the least two first conductive element portions comprise a pair of first conductive element portions that are configured to operate with opposite polarities.

18. The flexible circuit arrangement of claim 17, wherein the pair of first conductive element portions are configured to operate as separate pathways for current transmission in a DC circuit.

19. A flexible circuit module, comprising:
- an electrically insulating substrate;
- a conductive layer positioned on the substrate, wherein the conductive layer comprises at least two conductive elements positioned along a path between a first node and a second node in the conductive layer, wherein the first node and the second node are located at different positions on the substrate, wherein the at least two conductive elements are electrically coupled to the first node and the second node, and wherein the at least two conductive elements are electrically insulated from each other along the path between the first node and the second node;
- an electrically insulating top layer placed over the conductive layer on the substrate; and
- the at least two conductive elements comprising substantially flat, conductive wires made of conductive polymer.

20. The flexible circuit module of claim 19, wherein the conductive polymer is metal rubber.

* * * * *